(12) United States Patent
Chan

(10) Patent No.: US 7,029,883 B2
(45) Date of Patent: Apr. 18, 2006

(54) **PREPARATION OF AN *AURICULARIA AURICULA* POLYSACCHARIDE AND ITS USE IN MAMMALS**

(75) Inventor: Sun Sun Chan, Hong Kong (CN)

(73) Assignee: Eastmedicine Limited, Hong Kong (CN)

( * ) Notice: Subject to any disclaimer, the term of this patent is extended or adjusted under 35 U.S.C. 154(b) by 163 days.

(21) Appl. No.: 10/161,825

(22) Filed: Jun. 4, 2002

(65) Prior Publication Data

US 2003/0225001 A1 Dec. 4, 2003

(51) Int. Cl.
*C12P 19/04* (2006.01)
*C08B 37/00* (2006.01)

(52) U.S. Cl. ............... 435/101; 514/54; 536/123; 536/123.1; 536/123.12; 536/127

(58) Field of Classification Search ......... 435/101; 514/54; 536/123.1, 127, 123, 123.12
See application file for complete search history.

(56) References Cited

FOREIGN PATENT DOCUMENTS

JP 59-163323 * 9/1984

OTHER PUBLICATIONS

Zhang et al, Carbohydrate Res. 270:1-10, 1995.*
Kiho et al, Chem. Pharm. Bull. 39(3):798-800, 1991.*
Kiho et al, Carbohydrate Res. 142:344-351, 1985.*
Misaki et al, Carbohydrate Res. 92:115-129, 1981.*
Sone et al, Agric. Biol. Chem. 42(2):417-425, 1978.*

* cited by examiner

*Primary Examiner*—Francisco C. Prats
(74) *Attorney, Agent, or Firm*—Gibbons, Del Deo, Dolan, Griffinger & Vecchione

(57) ABSTRACT

A method for producing a purified *Auricularia auricula* Polysaccharide (AP) extract of *Auricularia auricula* (AA). A hydrated predetermined amount of AA is filtered and extracted, producing a first pre-extract. A plurality of additional hydrated predetermined amounts of AA is separately filtered and extracted to produce a plurality of additional pre-extracts. The pre-extracts are combined to form a first extract. The first extract is concentrated and suspended, forming a precipitate. The precipitate is purified to form a first filtrate, and repurified to form a second filtrate. The first and second filtrates are combined to form a first combined filtrate, which is concentrated, purified and dried to form a concentrated extract. The concentrated extract is purified to form a third filtrate, and repurified to form a fourth filtrate. The third and fourth filtrates are combined to obtain a second combined filtrate, which is concentrated, purified and dried to obtain the purified *Auricularia auricula* Polysaccharide extract of AA. A method of reducing the serum cholesterol in mammals by administering a pharmaceutically effective amount of the purified *Auricularia auricula* Polysaccharide (AP) extract of *Auricularia auricula* (AA) produced according to the foregoing method.

21 Claims, 1 Drawing Sheet

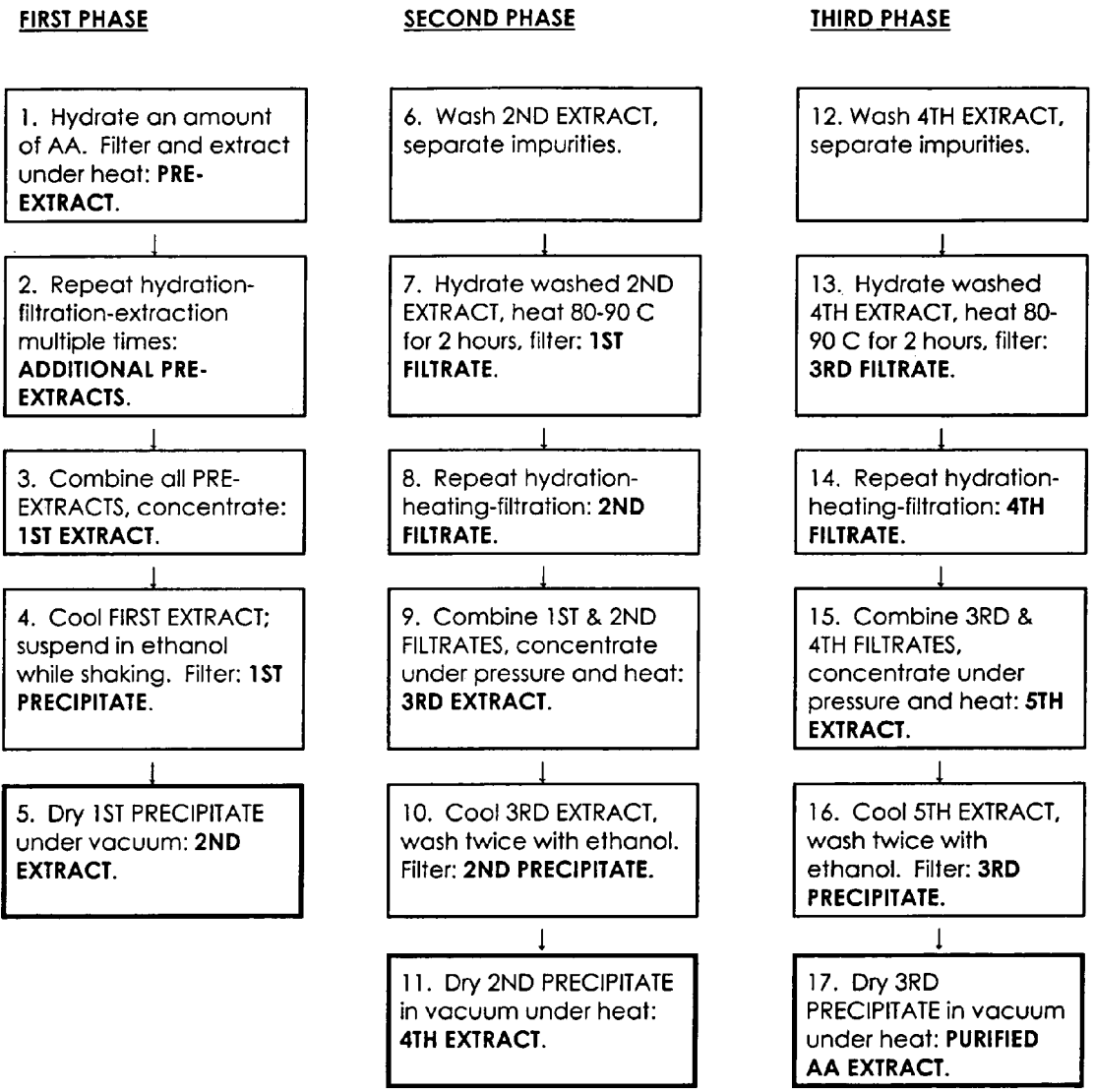

PREPARATION OF AN *AURICULARIA AURICULA* POLYSACCHARIDE AND ITS USE IN MAMMALS

FIELD OF THE INVENTION

The present invention pertains to the preparation of a specific extract of the *Auricularia auricula* wood fungus, and more particularly to the use of that extract for the lowering of cholesterol levels in humans.

BACKGROUND OF THE INVENTION

Cardiovascular disease (CVD) is a leading cause of death worldwide, particularly in developed nations. Many epidemiological studies show that an individual may lower their risk of CVD by lowering their cholesterol level. In fact, some of the world's leading drugs such as the statins (HMG CoA reductase) and fibrates have significantly reduced mortality in patients with CVD by lowering individual's cholesterol levels.

Naturally occurring supplements may also reduce mortality in patients with CVD. The therapeutic effects of *Auricularia Auricula* (AA), an edible wood fungus, are known. AA has been found to lower serum cholesterol levels, has been shown to exhibit anti-tumor properties, and also is known to be beneficial in the treatment of alloxan-induced diabetes.

Methods for aqueous extraction of AA also are known. Unfortunately, however, while many extraction methods for AA exist, most extracts are in the form of dilute aqueous solutions. Such solutions are hard to transport, store, and consume. Furthermore, mold formation readily affects the quality of these solutions. Most importantly, the clinical efficacy of these solutions is not satisfactory.

It would be beneficial, therefore, to provide a concentrated extract of AA in a capsule form. This capsule form can have greater clinical efficacy, improve the absorption of AA into the body, and establish proven health cholesterol lowering benefits.

What is needed is a method for aqueous extraction of AA whereby the extract is sufficiently concentrated to be useful in the lowering of serum cholesterol levels. What also is needed is an extract which is easy to transport, store and consume, and is less susceptible to mold and other contaminants.

Accordingly, the present invention provides a novel method for aqueous extraction of AA, resulting in a dried extract of *Auricularia auricula* polysaccharide that is easily incorporated into capsules, thereby increasing its ability to be stored for extended periods of time. The present invention also provides a method for lowering the serum cholesterol level in humans through administration of the AA extract.

SUMMARY OF THE INVENTION

The present invention is directed to a method for obtaining a purified *Auricularia auricula* polysaccharide (AP) extract of *Auricularia auricula* (AA).

In a preferred embodiment, a hydrated predetermined amount of AA is filtered and extracted, producing a first pre-extract. A plurality of additional hydrated predetermined amounts of AA is separately filtered and extracted to produce a plurality of additional pre-extracts. The pre-extracts are combined to form a first extract.

The first extract is concentrated and suspended, forming a precipitate. The precipitate is purified to form a first filtrate, and repurified to form a second filtrate. The first and second filtrates are combined to form a first combined filtrate, which is concentrated, purified and dried to form a concentrated extract.

The concentrated extract is purified to form a third filtrate, and repurified to form a fourth filtrate. The third and fourth filtrates are combined to obtain a second combined filtrate, which is concentrated, purified and dried to obtain the purified *Auricularia auricula* Polysaccharide extract of AA.

The invention further is drawn to a method of reducing serum cholesterol in mammals by administering a pharmaceutically effective amount of the purified extract obtained by the above method. In a preferred embodiment, this amount is administered in the form of a capsule, which further includes excipients such as L-hydroxypropylcellulose, microcrystalline cellulose, hexadecanol and 95% ethanol.

BRIEF DESCRIPTION OF THE DRAWING

The drawing is a flow chart showing the steps in the method of the present invention.

DETAILED DESCRIPTION OF THE INVENTION

*Auricularia auricula* polysaccharide (AP) is a purified extract of *Auricularia auricula* (AA). The molecular structure of AP consists of one acidic complex polysaccharide peptide, one water-soluble poly D-glucose peptide and one highly branched poly D-glucose-peptide joined together by β linkage as follows:

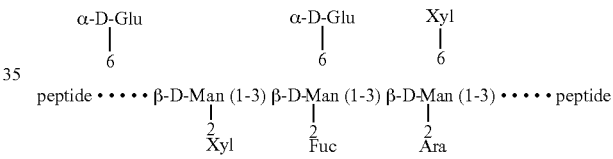

where Glu: Glucose; Man: Mannose; Xyl: Xylose; Fuc: Fucose; Ara: Arabinose

AP has been shown to be a pure preparation of polysaccharide peptide by spectral analyses, which showed multiple absorption in the infrared (IR) 400 range for polysaccharides. Spectral analyses showed no absorption peaks at ultraviolet (UV) 300 nm for nucleic acids nor any discrete peaks at UV 280 nm for protein. The monosaccharide composition of AP is as follows: L-fucose, L-arabinose, D-xylose, D-mannose, D-glucose, and Glucuronic acid in a molar ratio of 0.14:0.045:0.17:1.00:0.61:0.44, with a sugar content of 81.15%. The molecular weight of AP was determined to be 155000.

Clinical studies have shown the efficacy of AP in lowering serum lipids in humans. Specifically, a multi-center study established the beneficial effect in humans of AP on lowering total cholesterol (TC) and triglyceride (TG) levels, as well as increasing the level of high density lipoprotein cholesterol (HDL-C).

EXAMPLE 1

Effect of AP on Serum Total Cholesterol and Triglycerides in Humans

A multicenter study, based on the Fujian Traditional Chinese Medicine Research Institute protocol, involved 476 patients between November 1994 and August 1996. The study was conducted as a double-blind random trial, with 316 patients assigned to the AP group, and 160 patients assigned to the Fenofibrate (FF) (control) group. FF was chosen for the control group due to its known anithyperlipidemic properties.

The total patient population was approximately 61% male, with the AP group being approximately 60% male and the control group approximately 64% male. Patients in each group were 30–50 years old and averaged approximately 54–55 years of age. 164 patients had total cholesterol (TC) levels of 6.5–8.0 mmol/L, and 275 patients had triglycerides (TG) levels of 1.6–3.0 mmol/L. 131 patients had low high density lipoprotein (HDL) (<1.04 mmole/L for male, HDL<1.17 mmol/L for female). 201 patients had raised TC/HDL ratios (>5).

Patients with liver, renal and thyroid disease, as well as pregnant women and those who were on medications that could affect serum lipid readings, were excluded. Also excluded were patients who within the last year had had acute myocardial infarction, cerebral vascular diseases, major trauma and/or major surgery, as well as those with severe coronary or renal failure.

Patients in the test group received 3 200 mg capsules of AP and a matched FF placebo tablet. Patients in the control group received 3 capsules of matched placebo AP and a 100 mg tablet of FF. All medications were taken 2 times daily for 8 weeks. Although medications were administered by capsules, it should be understood that medications could be administered by tablets, liquids and/or pills as well.

The results are set forth in the following tables:

TABLE 1

Effect of AP on total cholesterol (TC)

| Group | No. | Start TC (mmol/L) | End TC (mmol/L) | Range of decreases (mmol/L) | P value |
|---|---|---|---|---|---|
| AP | 164 | 7.91 ± 1.65 | 6.27 ± 1.30 | 1.64 ± 1.16 | <0.01 |
| FF | 80 | 7.81 ± 1.38 | 6.46 ± 1.33 | 1.35 ± 1.05 | <0.01 |

TABLE 2

Effect of AP on triglyceride (TG) level

| Group | No. | Start TC (mmol/L) | End TC (mmol/L) | Range of decreases (mmol/L) | P value |
|---|---|---|---|---|---|
| AP | 275 | 3.12 ± 1.67 | 2.05 ± 0.95 | 1.07 ± 1.21 | <0.01 |
| FF | 143 | 2.94 ± 1.38 | 1.96 ± 1.10 | 0.98 ± 1.05 | <0.01 |

TABLE 3

Effect of AP on HDL level

| Group | No. | Start HDL (mmol/L) | End HDL (mmol/L) | Range of decreases (mmol/L) | P value |
|---|---|---|---|---|---|
| AP | 131 | 0.90 ± 0.19 | 1.11 ± 0.25 | 0.21 ± 0.25 | <0.01 |
| FF | 65 | 0.88 ± 0.27 | 1.06 ± 0.27 | 0.18 ± 0.15 | <0.01 |

TABLE 4

Effect of AP on TC/HDL ratio

| Group | No. | Start ratio | End ratio | Range of decreases (mmol/L) | P value |
|---|---|---|---|---|---|
| AP | 201 | 7.43 ± 2.49 | 4.79 ± 1.78 | 2.64 ± 1.89 | <0.01 |
| FF | 97 | 7.21 ± 1.95 | 5.16 ± 1.51 | 2.05 ± 1.41 | <0.01 |

TABLE 5

Summary of results

|  | AP | FF |
|---|---|---|
| Reduction in TC | 20.7%* | 17.3%* |
| Reduction in TG | 34.3%** | 33.3%** |
| Increase in HDL | 23.3%*** | 20.5%*** |

Based on the foregoing results, AP is effective in lowering TC and TG levels, as well as the TC/HDL ratio. AP also is effective in raising HDL levels. The effects were comparable to those for FF, with known antihyperlipidemic properties. AP achieved a 20.7% reduction in total cholesterol (TC), 35.5% in the ratio of total cholesterol to high density lipoprotein cholesterol (TC/HDL-C), and 34.3% in TG, compared to FF's 17.3%, 28.4% and 33.3%, respectively. Moreover, AP increased HDL-C by 23.3%, compared to 20.5% by FF.

Accordingly, AP is an effective antihyperlipidemic drug in humans.

Animal trials show similar results. Indeed, four studies of the effect of AP on lipid levels, total cholesterol (TC), free cholesterol (FC), cholesterol ester (Ch E), triglycerides (TG) and/or β-lipoprotein (β-LP) in rats or mice confirm the beneficial effects of AP.

EXAMPLE 2

Effect of AP on Serum TC in Mice With Hypercholesterolemia

Healthy Kunming mice were separated randomly into five groups, one of these serving as control. After fasting, the non-control groups were given an intraperitoneal infusion of high cholesterol feed. One of these groups served as the test control. Each of the remaining three groups was given AP 180 mg/kg intra gastric at 13, 16 or 19 hours post-infusion. Blood was drawn for TC determination at 1, 4 and 7 hours after intra gastric AP. The results are shown in Table 1.

TABLE 6

| Group | Dose (mg/kg) | No. mice | TC (mg/dl) |
|---|---|---|---|
| Control |  | 16 | 89.18 ± 18.18 |
| Test Control |  | 9 | 932.53 ± 329.39 |
| AP 1 hour | 180 | 10 | 909.99 ± 431.87 |
| AP 4 hours | 180 | 9 | 591.99 ± 210.12 |
| AP 7 hours | 180 | 8 | 702.28 ± 280.53 |

The results show that TC lowering effects appear at 1 hour after AP infusion, with statistically significant TC lowering effects occurring at 4 hours, and beginning to taper off by hour 7.

EXAMPLE 3

Dosage Strength and AP Effect on Serum TC of Hypercholesterolemic Mice

Healthy Kunming mice were randomly separated into 5 groups, one group acting as control. One group was given high cholesterol feed and acted as the test control. The remaining groups were given high cholesterol feeds and AP. After fasting, IP infusion of high cholesterol feed was given to the test control and test groups. The test groups were given AP intra gastric at 60, 120 and 180 mg/kg. Blood was drawn 4 hours later, and TC measured. The results are set forth in Table 2.

TABLE 7

| Group | Dose (mg/kg) | No. mice | TC (mg/dl) |
| --- | --- | --- | --- |
| Control | | 16 | 89.16 ± 18.18 |
| Test control | | 8 | 318.83 ± 140.88 |
| AP | 60 | 7 | 349.98 ± 60.19 |
| AP | 120 | 8 | 322.56 ± 112.44 |
| AP | 180 | 8 | 199.23 ± (69.59) |

The results show statistically significant cholesterol lowering effect at AP 180 mg/kg.

EXAMPLE 4

Prevention Effect of AP on Hypercholesterolemia in Serum of Mice

Healthy Kunmig mice were randomly separated into 6 groups, one being control. The remaining groups were test groups. After fasting, one test group (test control) was given an intra gastric infusion of normal saline. The remaining test groups were given ig AP at 6.7, 20, 60, and 120 mg/kg, respectively. 2 hours later, all five test groups were given IP high cholesterol feed. Blood was taken 20 hours later, and TC measured. The results are shown in Table 3.

TABLE 8

| Group | Dose (mg/kg) | No. mice | TC (mg/dL) |
| --- | --- | --- | --- |
| Control | | 16 | 89.18 ± 18.18 |
| Test control | | 8 | 797.06 ± 54.61 |
| AP | 6.7 | 8 | 667.32 ± 183.54 |
| AP | 20 | 7 | 494.44 ± 97.39 |
| AP | 60 | 8 | 488.95 ± 68.36 |
| AP | 120 | 8 | 356.84 ± 108.86 |

The results show prevention effects at 20, 60 and 120 mg/kg dosage levels.

EXAMPLE 5

AP Effect on Serum TC, FC, Ch E, TG and β-LP in Hyperlipidemicrats

Winstar rats were randomly assigned to three groups, one acting as control and one as test control. The third group was the AP test group. Control and test control groups were fed ig normal saline every morning for 8 days. Test group was given ig AP 28 mg/kg daily for 8 days. Other than control group, all rats were given high cholesterol feed. On the 9th day, after fasting, intracardiac blood was drawn from all animals, and TC, FC, Ch E, TG and β-LP measured. The results are set forth in Table 4.

TABLE 9

| Group | Dose (mg/kg) | No. mice | TC (mg/dl) | FC (mg/dl) | Ch E (mg/dl) | TC (mg/dl) | β-LP (mg/dl) |
| --- | --- | --- | --- | --- | --- | --- | --- |
| Control | | 13 | 57.29 ± 11.01 | 13.54 ± 3.56 | 46.30 ± 8.67 | 101.43 ± 25.44 | 288.03 ± 83.15 |
| Test Control | | 10 | 468.29 ± 141.68 | 95.57 ± 32.22 | 354.47 ± 111.45 | 138.00 ± 31.40 | 1097.98 ± 227.46 |
| AP | 28 | 7 | 308.14 ± 68.39 | 61.93 ± 7.97 | 264.22 ± 70.19 | 96.39 ± 15.97 | 842.34 ± 120.35 |

AP significantly lowered serum TC, FC, Ch E, TC and β-LP.

The purified extract of AA (AP) is obtained as follows: a predetermined amount of AA is hydrated, preferably with 30–80 fold (w/w) of water. The aqueous mixture is filtered and extracted under heat, preferably at 70–98° C., to produce a pre-extract. The steps of hydration and filtration/extraction are repeated to produce a plurality of additional pre-extracts, which are combined, along with the first of such pre-extracts. The combined pre-extracts are concentrated to form a concentrated first extract, which is cooled to room temperature and then suspended in ethanol (preferably 2–5 fold (w/w)), while shaking, with the particulate matter allowed to settle as a precipitate. In a preferred embodiment, the step of concentrating occurs at a pressure of 60–80 kPa and a temperature of 60–80° C.

The precipitate is washed with ethanol, preferably 95% ethanol, and dried in a vacuum. An amount of this dried extract (preferably with a sugar content not less than 40 g) is washed in 95% ethanol at 90° C. for 120 minutes, and the impurities are separated therefrom, forming a purified second extract. The so-purified second extract is hydrated (preferably in 50-fold (w/w) water) and heated at 80–90° C. for two hours, and the heated extract is filtered to obtain a filtrate. The cooked-and-filtered extract is then re-hydrated, cooked again, and filtered to obtain another filtrate. The filtrates are combined and concentrated under pressure (preferably 60–80 kPa) and heat (preferably 70° C.) to form a concentrated third extract. Preferably, the relative density of this third extract is 1.01–1.20 g/cm³. This extract is cooled and washed twice with ethanol (preferably 95%), while stirring, and the ethanol is filtered off. The washed and concentrated third extract is dried in a vacuum under heat (preferably 65° C.). The extract yield is >15%, with a water content <5%.

An amount of this dried extract (sugar content preferably not less than 45 g) is washed in 95% ethanol at 90° C. for 120 minutes, and the impurities separated therefrom, forming a purified fourth extract. The so-purified fourth extract is hydrated (preferably 50-fold (w/w)) and cooked at 80–90° C. for two hours, and the cooked extract is filtered to obtain a third filtrate. The cooked-and-filtered extract is re-hydrated, cooked again, and filtered to obtain a fourth filtrate. These filtrates are combined and concentrated under pressure (preferably 60–80 kPa) and heat (preferably 70° C.) to form a concentrated fifth extract having a relative density preferably of 1.1 g/cm$^3$. This extract is cooled and washed twice with ethanol (preferably 95%, preferably 3-fold (w/w)), while stirring, and the ethanol is filtered off. The washed concentrated fifth extract is then dried in a vacuum under heat (preferably 65° C.) to obtain a purified extract of *Auricularia Auricula*. Yield of the purified extract is >15%, with a water content <5%

The purified extract of AA (AP) can be incorporated into capsules as follows: an amount, preferably 200 g, of the dried AA extract is ground into small pieces. The small pieces are mixed with 12.5 g of L-hydroxypropylcellulose and 20 g of microcrystalline cellulose. 17.25 g of hexadecanol is added, as well as an insignificant amount of ethanol. 150 ml of warm 95% ethanol is then added to dissolve the mixture completely. 1000 capsules are then filled with the mixed solution and are allowed to dry at 60° C. Each capsule will contain the following ingredients: 200 mg of AA, 20 mg of microcrystalline cellulose, 12.5 mg of L-hydroxypropylcellulose, 17.25 mg of hexadecanol and an insignificant amount of ethanol. Based on the above-described research, a capsule containing such an amount of the AA extract of the present invention will be efficacious in reducing the serum cholesterol of humans.

While the invention has been described with respect to certain specific embodiments, it will be appreciated that many modifications and changes may be made by those skilled in the art without departing from the invention. It is intended, therefore, by the appended claims to cover all such modifications and changes as may all within the true spirit and scope of the invention.

What is claimed is:

1. A method of producing a purified *Auricularia Auricula* Polysaccharide (AP) extract of *Auricularia Auricula* (AA), comprising the steps of:
   a. filtering and extracting a hydrated predetermined amount of AA to produce a first pre-extract;
   b. separately filtering and extracting each of a plurality of additional hydrated predetermined amounts of AA to produce a plurality of additional pre-extracts;
   c. combining said first pre-extract with said plurality of additional pre-extracts to form a first extract;
   d. concentrating and suspending said first extract to form a precipitate;
   e. filtering said precipitate to form a first filtrate;
   f. refiltering said precipitate to form a second filtrate;
   g. combining said first filtrate with said second filtrate to obtain a first combined filtrate;
   h. concentrating and drying said first combined filtrate to form a concentrated extract;
   i. filtering said concentrated extract to form a third filtrate;
   j. refiltering said concentrated extract to form a fourth filtrate;
   k. combining said third filtrate with said fourth filtrate to obtain a second combined filtrate;
   l. concentrating and drying said second combined filtrate to obtain said purified *Auricularia Auricula* Polysaccharide extract of *Auricularia Auricula*.

2. The method of claim 1, wherein the step of separately filtering and extracting each of a plurality of additional hydrated predetermined amounts of AA takes place at approximately 70–98° C.

3. The method of claim 1, wherein the step of concentrating and suspending said first extract comprises the steps of concentrating said first extract, suspending said concentrated first extract, with shaking, and allowing particulate matter formed thereby to settle as a precipitate.

4. The method of claim 3, wherein the step of suspending said concentrated first extract occurs in the presence of ethanol.

5. The method of claim 3, wherein the step of concentrating said first extract occurs at approximately 60–80° C. and 60–80 kPa.

6. The method of claim 4, wherein the step of suspending said concentrated first extract occurs in 2–5 fold (w/w) ethanol.

7. The method of claim 1, wherein step e comprises the steps of washing said precipitate with ethanol, drying said washed precipitate in a vacuum, hydrating said washed and dried precipitate, cooking said washed, dried and hydrated precipitate, and filtering said cooked, washed, dried and hydrated precipitate.

8. The method of claim 7, wherein the step of washing said precipitate occurs in the presence of 90% ethanol.

9. The method of claim 7, wherein the step of cooking said washed, dried and hydrated precipitate occurs at approximately 80–90° C. for 2 hours.

10. The method of claim 1, wherein step f comprises the steps of rehydrating said precipitate, after said filtering cooking said rehydrated filtered precipitate, and filtering said cooked, rehydrated filtrate.

11. The method of claim 10, wherein the step of cooking said rehydrated filtered precipitate occurs at approximately 80–90° C. for 2 hours.

12. The method of claim 1, wherein step h comprises the steps of concentrating said first combined filtrate, washing said concentrated first combined filtrate with ethanol and stirring, filtering said ethanol from said washed concentrated first combined filtrate, and drying said filtered, washed concentrated first combined filtrate in a vacuum.

13. The method of claim 12, wherein the step of concentrating said first combined filtrate occurs at approximately 60–80 kPa and 70° C. for 120 minutes.

14. The method of claim 12, wherein the step of drying said filtered, washed concentrated first combined filtrate in a vacuum takes place at approximately 65° C.

15. The method of claim 1, wherein step l comprises the steps of concentrating said second combined filtrate, washing said concentrated second combined filtrate with ethanol and stirring, filtering said ethanol from said washed concentrated second combined filtrate, and drying said filtered, washed concentrated second combined filtrate in a vacuum.

16. The method of claim 15, wherein the step of concentrating said second combined filtrate occurs at approximately 60–80 kPa and 70° C. for 120 minutes.

17. The method of claim 15, wherein the step of drying said filtered, washed concentrated second combined filtrate in a vacuum takes place at approximately 65° C.

18. A method of producing a purified *Auricularia Auricula* Polysaccharide (AP) extract of *Auricularia Auricula* (AA) and reducing serum cholesterol in mammals, the method comprising the steps of:
   (a) preparing the *Auricularia Auricula* polysaccharide extract by the method of claim 1, and
   (b) administering a pharmaceutically effective amount of the purified extract of *Auricularia Auricula* to a mammal.

19. The method of claim 18 wherein said pharmaceutically effective amount of the purified extract of *Auricularia Auricula* is administered in the form selected from the group consisting of capsules, tablets, liquids and pills.

20. The method of claim 19 wherein said capsule further comprises excipients selected from the group consisting of: L-hydroxypropylcellulose, microcrystalline cellulose, hexadecanol and 95% ethanol.

21. The method of claim 18, wherein the mammal is a human.

* * * * *